United States Patent [19]

White et al.

[11] 4,136,110

[45] Jan. 23, 1979

[54] PROCESS FOR THE PREPARATION OF UNSATURATED ACIDS FROM UNSATURATED ALDEHYDES

[75] Inventors: James F. White, Akron; James R. Rege, Lakewood, both of Ohio

[73] Assignee: The Standard Oil Company, Cleveland, Ohio

[21] Appl. No.: 763,775

[22] Filed: Jan. 31, 1977

Related U.S. Application Data

[63] Continuation-in-part of Ser. No. 605,363, Aug. 18, 1975, abandoned.

[51] Int. Cl.$^2$ .............................................. C07C 51/32
[52] U.S. Cl. .................................... 562/532; 252/435; 252/437
[58] Field of Search ................... 260/530 N; 252/435, 252/437

[56] References Cited

U.S. PATENT DOCUMENTS

| | | | |
|---|---|---|---|
| 3,795,703 | 3/1974 | Nuna et al. | 260/530 N |
| 3,865,873 | 2/1975 | Ada et al. | 260/530 N |
| 3,928,240 | 12/1975 | Milberger et al. | 260/530 N |

FOREIGN PATENT DOCUMENTS

| | | | |
|---|---|---|---|
| 47-33082 | 11/1972 | Japan | 260/530 N |

*Primary Examiner*—Vivian Garner
*Attorney, Agent, or Firm*—Gwenetta Douglas Hill; Herbert D. Knudsen; Larry W. Evans

[57] ABSTRACT

Methacrylic acid or acrylic acid is produced by the oxidation of methacrolein or acrolein respectively, with molecular oxygen in the vapor phase in the presence of a catalytic oxide of molybdenum and phosphorus, promoted with chromium or at least one element selected from the group consisting of thallium, rubidium, cesium, potassium, titanium, and arsenic, or a mixture thereof, wherein at least part of the molybdenum employed in the preparation of the catalyst is supplied in the form of molybdenum trioxide. The oxidation of methacrolein in the presence of a catalyst wherein all the molybdenum employed in the preparation of the catalyst has been supplied by molybdenum trioxide gives especially desirable high yields and selectivities to methacrylic acid.

10 Claims, No Drawings

PROCESS FOR THE PREPARATION OF UNSATURATED ACIDS FROM UNSATURATED ALDEHYDES

REFERENCE TO RELATED APPLICATIONS

This is a continuation-in-part of our earlier application, U.S. Ser. No. 605,363, filed Aug. 18, 1975, abandoned.

BACKGROUND OF THE INVENTION

U.S. Pat. No. 2,865,873, U.S. 3,882,047 and Japanese Pat. No. 47-33082 disclose catalysts that are useful in the oxidation of unsaturated aldehydes to unsaturated acids, wherein ammonia or an ammonium-containing compound is incorporated in the preparation of the catalysts.

U.S. Pat. No. 2,865,873 in Column 13, Examples 101 to 104 discloses a process for the preparation of methacrylic acid using catalysts consisting of molybdenum, phosphorus, titanium and oxygen, wherein ammonium paramolybdate is employed in the preparation of the catalysts. The highest yield of methacrylic acid produced is about 39.56%.

U.S. Pat. No. 3,882,047 discloses the preparation of methacrylic acid using catalysts containing molybdenum, phosphorus, at least one element such as thallium, rubidium, cesium and potassium, and at least one element such as chromium, silicon, aluminum, iron and titanium. This reference teaches the incorporation of ammonia or ammonium-containing compounds in the preparation of all catalysts exemplified in the oxidation of methacrolein or acrolein; phosphomolybdic acid is employed in the preparation of virtually all catalysts exemplified; and in a few examples, ammonia molybdate is employed. This patent discloses in Column 3, lines 30–40 as follows:

"It is preferred that the catalyst be prepared so that the constituent elements will form complex compounds such as heteropolyacids, then acid salts or ammonium salts."

Japanese Pat. No. 47-33082 discloses a process for reclaiming an ammonia-modified phosphorus-molybdenum-X-oxygen catalyst, wherein X is at least one element selected from the group consisting of As, Bi, Si, Cd, W, Tl, Pb, Ge, In, Sn, Sb, and Fe. Preparation of the catalyst involves treating the catalyst with ammonia and water by oxidizing the catalyst in advance or by oxidizing it simultaneously with the treatment of ammonia and water. This patent discloses that the ammonia forms a complex compound with the other elements present.

The present invention is the result of a search for more efficient catalysts for use in the oxidation of acrolein or methacrolein to produce acrylic acid or methacrylic acid, respectively. By the process of the present invention (1) higher yields of methacrylic acid are produced as compared with the art processes; (2) calcination of the catalysts is not required; (3) catalysts are prepared from molybdenum trioxide; and (4) catalysts are prepared in the absence of ammonia or an ammonium-containing compound.

SUMMARY OF THE INVENTION

It has now been discovered according to the present invention in the process for the preparation of acrylic acid or methacrylic acid by the oxidation of acrolein or methacrolein respectively, with molecular oxygen in the vapor phase at a reaction temperature of about 200° C. to about 500° C. in the presence of an oxide catalyst, and optionally in the presence of steam, the improvement comprising using as a catalyst a catalyst described by the empirical formula $$A_aCr_bMo_3P_cO_x$$

wherein A is at least one of the elements selected from the group consisting of rubidium, thallium, cesium, arsenic, titanium and potassium;
and wherein a is a positive number less than about 3;
b is zero to about 3;
c is a positive number less than about 2;
x is the number of oxygens required by the valence states of the other elements present;
and wherein at least part of the molybdenum employed in the preparation of the catalyst is supplied in the form of molybdenum trioxide.

Preferred catalysts are described by the formula $$A_aMo_3P_cO_x$$

wherein A is at least one element selected from the group consisting of rubidium, cesium, thallium, and potassium;
wherein a is a positive number less than about 3;
c is a positive number less than about 2;
x is the number of oxygens required by the valence states of the other elements present;
wherein said oxide catalyst is prepared in a refluxed aqueous slurry of molybdenum trioxide, wherein molybdenum trioxide is the source of all the molybdenum employed in the preparation of the catalyst; and wherein said catalyst is prepared in the absence of ammonia or a compound containing ammonium.

Also preferred are catalysts containing titanium, molybdenum, phosphorus and oxygen.

Unexpected improvements are achieved in yields of acrylic acid and methacrylic acid by the use of the catalysts of the present invention wherein molybdenum trioxide is incorporated into the preparation of the catalysts as compared to results obtained with the art catalysts prepared from phosphomolybdic acid.

The most important aspect of the present invention is the preparation of the catalyst employed. The incorporation of molybdenum trioxide into the catalyst preparations is critical to the present invention. The central feature is the fact that the stability, activity and selectivity of the catalyst are significantly enhanced when at least part of the molybdenum employed in the catalyst preparations is supplied in the form of molybdenum trioxide.

By the preferred procedure of the invention, molybdenum trioxide must supply at least 25% of the molybdenum employed in the preparation of the catalysts. More preferred catalysts of the invention are described wherein at least 50% of the molybdenum employed in the preparation of the catalysts is supplied in the form of molybdenum trioxide.

However, the catalysts of greatest interest in the invention, whereby optimal results are obtained, are described wherein all the molybdenum employed in the preparation of the catalysts is supplied by molybdenum trioxide.

In the preparation of the catalysts of this invention, the methods of incorporating molybdenum trioxide may vary widely. A number of different techniques are known to those skilled in the art. The incorporation of molybdenum trioxide into the preparation of the catalysts may be before or after the addition of the remaining catalytic components.

The most preferred procedure of this invention involves the preparation of the catalysts in a refluxed aqueous slurry of molybdenum trioxide. Also preferred is the preparation of the catalysts in the absence of ammonia or an ammonium-containing compound.

As noted, the catalysts employed in the present invention may be any catalyst delineated by the above formula. The catalysts can be prepared by a number of different techniques known to those skilled in the art, such as coprecipitation of soluble salts, evaporative drying, or oxide mixing, followed by calcining the resulting catalysts. In the broad concept of the invention, the particular method of preparing the catalysts is not critical. By the preferred procedure of the invention, the catalysts are not calcined prior to being reacted with methacrolein or acrolein.

The preferred procedure of the present invention involves the refluxing of an aqueous slurry of molybdenum trioxide for 1.5 to 3 hours, followed by the addition of compounds containing phosphorus and the remaining catalytic components; boiling the aqueous mixture to a thick paste; drying at 110° C. to 120° C. in air; crushing and screening the resulting catalysts for testing. Soluble salts of the catalytic components other than molybdenum are preferred, however, insoluble salts or oxides may be used. Suitable phosphorus compounds that may be employed in the preparation of the catalysts include orthophosphoric acid, metaphosphoric acid, triphosphoric acid, phosphorus pentabromide, phosphorus pentachloride, and the like. The remaining catalytic components may be added as oxide, acetate, formate, sulfate, nitrate, carbonate, and the like.

Preferred catalysts of the invention are described wherein the preparation of the catalyst is accomplished by adding compounds containing phosphorus, chromium, and at least one element containing A to a refluxed aqueous slurry of molybdenum trioxide. More preferred catalysts are described wherein the preparation of the catalyst is accomplished by adding compounds containing phosphorus and at least one compound containing A to a refluxed aqueous slurry of molybdenum trioxide. However, the most preferred catalysts are described wherein the preparation of the catalyst is accomplished by adding compounds of phosphorus and at least one element selected from the group consisting of rubidium, cesium, and thallium.

The reactants of the reaction of the invention are acrolein or methacrolein and molecular oxygen. Molecular oxygen is normally supplied to the reaction in the form of air, but oxygen gas could also be employed. About 0.5 to about 10 moles of oxygen are normally added per mole of acrolein or methacrolein.

Optionally added to the reactants is steam or an inert diluent. Preferred reactions are conducted in the presence of substantial quantities of steam in the range of about 2 to about 20 moles of steam per mole of acrolein or methacrolein.

The reaction temperature may vary as different catalysts are employed. Normally, temperatures of about 200° C. to about 500° C. are employed with temperatures of about 250° C. to about 400° C. being preferred.

The reaction may be conveniently conducted in either a fixed-bed or fluid-bed reactor. The contact time may be as low as a fraction of a second or as high as 20 seconds or more, the preferred contact time is 4 to 5 seconds. The reaction may be conducted at atmospheric, superatmospheric of subatmospheric pressure, with absolute pressures of about 0.5 to about 4 atmospheres being preferred.

When used in the reactor, the catalyst may be in a supported or unsupported form. Suitable support materials include silica, alumina, boron, phosphate, zirconia, titanium and the like, but the most preferred is zirconia.

The examples below are representative of the catalyst preparations that are suitable for the process of this invention, however, the scope of the invention is not limited to these examples. The preferred reaction of the invention is the oxidation of methacrolein to methacrylic acid. Of course, acrolein can be converted to acrylic acid using the catalysts and techniques of the present invention.

SPECIFIC EMBODIMENTS

EXAMPLE 1, COMPARATIVE EXAMPLES A, B, AND C

Production of methacrylic acid using a catalyst, $Rb_{0.5}Mo_3P_{0.33}O_x$, prepared from molybdenum trioxide compared with using this catalyst prepared from different sources of molybdenum Preparation and use of this catalyst are as follows:

EXAMPLE 1 — PREPARATION FROM MOLYBDENUM TRIOXIDE.

An aqueous slurry was prepared by adding 55.3 g. of molybdenum trioxide to one liter of boiling distilled water with stirring; the slurry was boiled for about 2 hours. To this aqueous slurry, 4.9 g. of 85% phosphoric acid was added, the color of the slurry changed to yellow. About 200 ml. of distilled water was added to maintain an approximately 800 mls. solution level. About 1½ hours after the addition of 85% phosphoric acid, the color of the slurry changed to a pronounced yellow-green; then 100 mls. of distilled water was added to maintain solution level. To this aqueous mixture, 7.5 g. of rubidium carbonate were added; the color of the slurry became bright yellow; after about 30 minutes 25 mls. of distilled water were added. The catalyst was heated with stirring; boiled to dryness; and dried in air at about 110° C.

COMPARATIVE EXAMPLE A — PREPARATION FROM PHOSPHOMOLYBDIC ACID.

An aqueous solution was prepared by dissolving 118.3 g. of phosphomolybdic acid in about 1400 mls. of distilled water. To this solution, 1.92 g. of 85% phosphoric acid was added. The pale yellow solution was boiled for about eight hours; stirred without heating for 12 hours. Heating was resumed, 11.6 g. of rubidium carbonate was added and the color of the solution changed rapidly to bright yellow. The aqueous mixture was boiled to dryness; dried in air at 110° C. overnight.

COMPARATIVE EXAMPLE B — PREPARATION FROM AMMONIUM HEPTAMOLYBDATE.

A slurry consisting of 105.9 g. of ammonium heptamolybdate, $(NH_4)_6Mo_7O_{24}\cdot 4H_2O$, 7.7 g. of 85% phosphoric acid and 1400 mls. of distilled water was boiled with stirring. The color of the slurry changed slowly from pale yellow to white. After boiling, the slurry was stirred without heating for 12 hours. Heating was resumed, and 11.6 g. of rubidium carbonate was added; the color of the aqueous mixture remained white. The aqueous mixture was boiled to dryness; dried in air at 110° C. overnight.

COMPARATIVE EXAMPLE C — PREPARATION FROM MOLYBDIC ACID.

Preparation of this catalyst was in the same manner as Comparative Example B, except 7.7 g. of 85% phosphoric acid were employed, and the ammonium heptamolybdate was replaced by 101.6 g. of molybdic acid.

The catalysts prepared in Example 1, Comparative Examples A, B and C were ground and screened to recover these particles of 20 to 30 mesh size. A portion of these catalyst particles was charged to a 20 cc. fixed-bed reactor consisting of a 1.3 cm. stainless steel tubing equipped with a 0.3 cm. axial thermowell. The reactor was heated to a reaction temperature of 343° C. under a flow of air and a feed of methacrolein/air/steam of 1/6.2/5.2 was fed over the catalyst at an apparent contact time of 4.6 seconds.

In Comparative Examples B and C the catalysts were calcined at 430° C. for 1 hour, and then the temperature was reduced to 343° C. The reactor was run under the reaction conditions for 1.6 hours and then the product was collected by scrubbing the reactor off gases in two series water scrubbers. The scrubber contents were combined and diluted to 100 cc. for analysis and titration for acid content. The scrubbed fixed gases were dried and analyzed on a conventional Houdry split column system. The results of these experiments are shown in Table I below. The following definitions are used measuring the carbon atoms in the feed and the products.

$$\% \text{ Single pass Yield} = \frac{\text{Methacrylic Acid Recovered}}{\text{Methacrolein Feed}} \times 100$$

$$\% \text{ Conversion} = \frac{\text{Methacrolein Reacted}}{\text{Methacrolein Feed}} \times 100$$

$$\% \text{ Selectivity} = \frac{\text{Methacrylic Acid Recovered}}{\text{Methacrolein reacted}} \times 100$$

EXAMPLES 2-5 — EFFECT OF ON STREAM TIME ON CATALYTIC ACTIVITY USING THE CATALYST $Rb_{0.5}Mo_3P_{0.33}O_x$.

The catalyst prepared in accordance with Example 1 and reacted with methacrolein was left on stream for further determination of methacrolein conversion to methacrylic acid. The results of this experiment are shown in Table II.

TABLE I
PRODUCTION OF METHACRYLIC ACID USING THE CATALYST $Rb_{0.5}Mo_3P_{.33}O_x$ PREPARED FROM $MoO_3$ ACCORDING TO THE INVENTION COMPARED WITH THE PREPARATIONS FROM DIFFERENT SOURCES OF MOLYBDENUM

| | | Results, % | | |
|---|---|---|---|---|
| Example | Source of Molybdenum | Total Conversion | Single Pass Yield Methacrylic Acid | Selectivity |
| | Molybdenum trioxide | 97.9 | 62.2 | 63.5 |
| Comp. Ex. A | phosphomolybdic acid | 96.0 | 59.6 | 62.0 |
| Comp. Ex. B | ammonium heptamolybdate | 84.9 | 47.1 | 54.8 |
| *Comp. Ex. C | molybdic acid | 80.5 | 43.1 | 53.5 |

*on-stream 4.2 hrs.

TABLE II
THE EFFECT OF ON-STREAM TIME ON CATALYTIC ACTIVITY

| | | Results, % | | |
|---|---|---|---|---|
| Ex. | On-Stream Time, Hours | Total Conversion | Single Pass Yield Methacrylic Acid | Selectivity |
| 2 | 4.3 | 98.1 | 62.5 | 63.7 |
| 3 | 16.5 | 96.0 | 69.5 | 72.4 |
| 4 | 64.4 | 96.4 | 71.6 | 74.3 |
| 5 | 94.0 | 95.5 | 69.0 | 72.2 |

TABLE III
PREPARATION OF METHACRYLIC ACID FROM METHACROLEIN

| | | | Results, % | | |
|---|---|---|---|---|---|
| Example | Catalyst | Reaction Temperature, °C | Total Conversion | Single Pass Yield Methacrylic Acid | Selectivity |
| 6 | $Tl_{0.5}Mo_3P_{.33}O_x$ | 343 | 91.9 | 51.0 | 54.4 |
| 7 | $Tl_{0.5}Mo_3P_{.33}O_x$ | 329 | 76.8 | 40.2 | 51.7 |
| 8 | $Cs_{0.5}Mo_3P_{.33}O_x$ | 343 | 98.8 | 58.2 | 58.9 |
| 9 | $K_{0.5}Mo_3P_{.33}O_x$ | 371 | 69.5 | 39.4 | 59.1 |
| 10 | $As_{0.5}Mo_3P_{.33}O_x$ | 355 | 78.0 | 56.0 | 76.0 |

We claim:

1. In a process for the preparation of acrylic acid or methacrylic acid by the oxidation of acrolein or methacrolein, respectively, with molecular oxygen in the vapor phase at a reaction temperature of about 200° C. to about 500° C. in the presence of an oxide catalyst, and optionally in the presence of steam, the improvement comprising using as the catalyst a catalyst of the formula:

$$A_aMo_3P_cO_x$$

wherein A is at least one element selected from the group consisting of rubidium, cesium, thallium, and potassium;
wherein a is a positive number less than about 3;
c is a positive number less than about 2;
x is the number of oxygens required by the valence state of the other elements present;

wherein said oxide catalyst is prepared in the absence of ammonia or a compound containing ammonium by:
(a) forming an aqueous slurry or suspension of molybdenum trioxide;
(b) refluxing the aqueous slurry or suspension and
(c) adding to the refluxed aqueous slurry or suspension at least one compound containing the phosphorus component and at least one compound containing the A component.

2. The process of claim 1 wherein said oxide catalyst is prepared in the absence of ammonia or a compound containing ammonium by:
(a) forming an aqueous slurry or suspension of molybdenum trioxide;
(b) refluxing the aqueous slurry or suspension;
(c) adding to the refluxed aqueous slurry or suspension at least one compound containing the phosphorus component and
(d) adding at least one compound containing the A component to the resulting refluxed slurry or suspension.

3. The process of claim 1 wherein A is rubidium.
4. The process of claim 1 wherein A is cesium.
5. The process of claim 1 wherein A is thallium.
6. The process of claim 1 wherein A is potassium.
7. The process of claim 1 wherein methacrolein is reacted.
8. The process of claim 1 wherein the catalyst prepared is $Rb_{0.5}Mo_3P_{0.33}O_x$.
9. In a process for the preparation of acrylic acid or methacrylic acid by the oxidation of acrolein or methacrolein, respectively, with molecular oxygen in the vapor phase at a reaction temperature of about 200° C. to about 500° C. in the presence of an oxide catalyst, and optionally in the presence of steam, the improvement comprising using as the catalyst a catalyst of the formula:

$$Ti_aMo_3P_cO_x$$

wherein a is a positive number less than about 3;
c is a positive number less than about 2;
x is the number of oxygens required by the valence states of the other elements present;
wherein said oxide catalyst is prepared in the absence of ammonia or a compound containing ammonium by:
(a) forming an aqueous slurry or suspension of molybdenum trioxide;
(b) refluxing the aqueous slurry or suspension and
(c) adding to the refluxed aqueous slurry or suspension at least one compound containing the phosphorus component and at least one compound containing the A component.

10. The process of claim 9 wherein said oxide catalyst is prepared in the absence of ammonia or a compound containing ammonium by:
(a) forming an aqueous slurry or suspension of molybdenum trioxide;
(b) refluxing the aqueous slurry or suspension;
(c) adding to the refluxed aqueous slurry or suspension at least one compound containing the phosphorus component;
(d) adding at least one compound containing the A component to the resulting refluxed slurry or suspension.

* * * * *